(12) United States Patent
Dietz et al.

(10) Patent No.: US 8,164,337 B2
(45) Date of Patent: Apr. 24, 2012

(54) ASSEMBLY WITH A VIBRATION-ISOLATED COVER

(75) Inventors: Peter Dietz, Fürth (DE); Annette Lohfink, Erlangen (DE); Bernd Maciejewski, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 929 days.

(21) Appl. No.: 12/221,666

(22) Filed: Aug. 5, 2008

(65) Prior Publication Data

US 2009/0044212 A1    Feb. 12, 2009

(30) Foreign Application Priority Data

Aug. 10, 2007   (DE) .................. 10 2007 037 851

(51) Int. Cl.
*G01V 3/00* (2006.01)
(52) U.S. Cl. .................................................. 324/318
(58) Field of Classification Search .................. None
See application file for complete search history.

(56) References Cited

U.S. PATENT DOCUMENTS

| 5,235,283 | A | 8/1993 | Lehne et al. | |
|---|---|---|---|---|
| 5,874,880 | A * | 2/1999 | Laskaris et al. | 335/216 |
| 6,552,543 | B1 | 4/2003 | Dietz | |
| 7,053,744 | B2 | 5/2006 | Arz et al. | |
| 7,071,693 | B2 * | 7/2006 | Yasuhara | 324/319 |
| 2003/0088172 | A1 * | 5/2003 | Kuth | 600/407 |
| 2006/0202695 | A1 * | 9/2006 | McDougall et al. | 324/318 |

FOREIGN PATENT DOCUMENTS

| DE | 4141514 A1 | 8/1992 |
|---|---|---|
| DE | 19838390 A1 | 3/2000 |
| DE | 19940551 C1 | 5/2001 |
| DE | 10147745 C2 | 7/2003 |
| WO | WO 03087862 A1 | 10/2003 |

\* cited by examiner

*Primary Examiner* — Roberto Velez

(57) ABSTRACT

An inventive vibration-generating device comprises a cover and isolating device arranged between the cover and the assembly. The isolating device reduces the propagation of vibrations from the vibration-generating assembly to the outer casing of the cover and is hereby supported according to the embodiment so that they float in relation to the assembly and/or the cover.

18 Claims, 3 Drawing Sheets

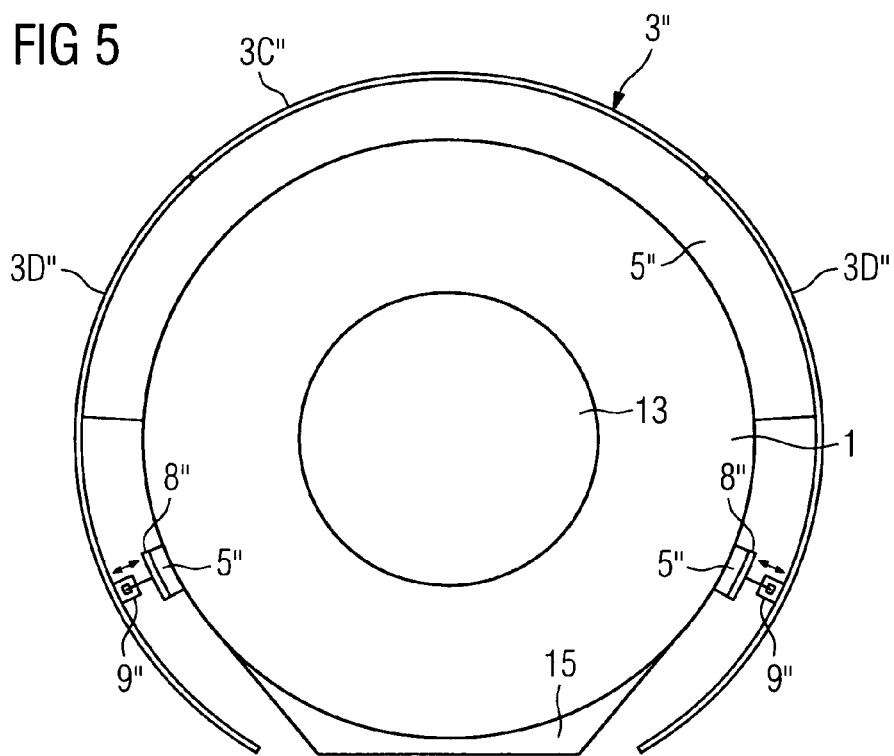
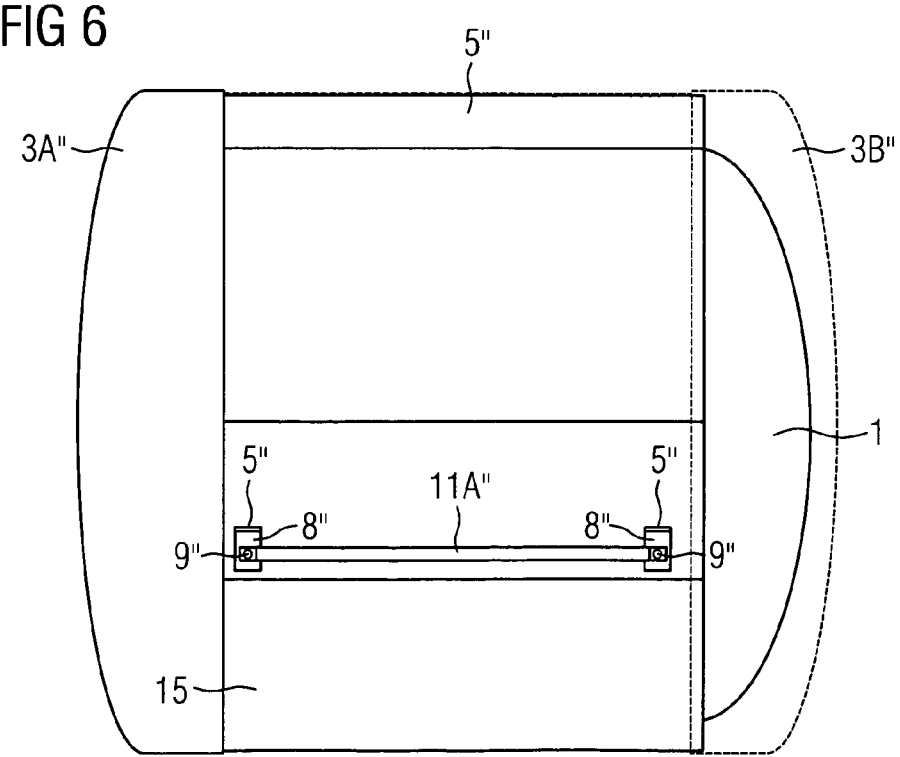

ASSEMBLY WITH A VIBRATION-ISOLATED COVER

CROSS REFERENCE TO RELATED APPLICATIONS

This application claims priority of German application No. 10 2007 037 851.5 filed Aug. 10, 2007, which is incorporated by reference herein in its entirety.

FIELD OF THE INVENTION

The invention relates to an assembly with a vibration-isolated cover.

BACKGROUND OF THE INVENTION

Assemblies, for example of known treatment and examination facilities, such as for example magnetic resonance systems, are enclosed by different cover parts to cover the facility on the outside. The cover hereby serves both to improve the appearance of the assembly and also to encapsulate the noise and provide protection against external influences, in particular for the electronic system of the assembly.

Cover parts are hereby secured permanently to the assemblies or modules, frequently with the aid of large frames or brackets. Such rigid systems for securing a cover to a vibration-generating assembly provide good acoustic conduction, resulting in poor acoustic characteristics for the facility as a whole. When the vibrations of an assembly are transmitted, for example to its cover, one transmission path is dominant. This preferably runs by way of direct mechanical connections, e.g. the rigid securing systems mentioned above, between the assembly and cover. Vibrations are thus transmitted to the cover and generate undesirably loud noise in the area around the facility. Also both the production and initial assembly of such frames take time and therefore also incur costs.

Magnetic units of magnetic resonance units for example, comprising a main magnet and gradient coils, generate vibrations in the magnet unit due to rapidly switching gradient currents in the gradient coils required for signal generation and these vibrations can cause significant noise problems.

DE 199 40 551 C1 already describes a magnetic resonance tomography unit, having an isolation device, which is arranged and configured so that the propagation of vibrations from a sub-region of a basic field magnet system of the magnetic resonance tomography device, originating from a vibration generator in the basic field magnet system, to at least a sub-region of an outer casing of the basic field magnet system, is prevented.

DE 101 47 745 C2 describes a nuclear spin tomography device in which noise is suppressed by damping mechanical vibrations, using active damping elements to damp the vibrations.

The devices used to date to damp vibrations are however each associated with high assembly outlay and/or costs.

SUMMARY OF THE INVENTION

The object of the invention is therefore to specify assemblies with a vibration-isolated cover, which are both economical and simple to produce and assemble and have low noise emissions.

The object is achieved by an inventive assembly as claimed in the claims.

Here a vibration-generating assembly comprises a cover and an isolating means arranged between the cover and the assembly. The isolating means reduce the propagation of vibrations from the vibration-generating assembly to the outer casing of the cover and are hereby supported so that they float in relation to the assembly and/or cover.

With an inventive assembly the excitation of vibrations at the cover by the vibration-generating assembly is damped to the greatest possible degree. The floating support of the isolating means prevents the establishment of dominant vibration transmission paths. At the same time the floating support allows simple and rapid assembly of the cover on the assembly.

A floating support here means that parts that are supported so that they float in relation to one another are not connected by means of rigid securing means, such as screws, rivets, adhesive or other securing means that adhere permanently to both parts, but are simply supported on top of one another. In this process either the weight of the topmost part or simple clamping forces, for example by means of a spring, ensure that the parts stay together and a rigid link and therefore sound bridges are avoided. This means that there is no permanent mechanical transmission path for sound and/or vibrations.

The isolating means are advantageously configured as large bearing surfaces on which the cover rests. Large, vibration isolating bearing surfaces between the assembly and the cover mean that vibration peaks and interference forming on the surface of the assembly can be equalized more easily than with just local isolating devices or those that only act on a very limited surface, as known from the prior art. Large, vibration-isolating bearing surfaces damp the vibration emission of the assembly surface effectively and no longer transmit it by way of local bridges, as the static load is better distributed. It is thus possible to use a softer material and isolation frequencies become lower. This makes isolation more effective. Such isolating means are advantageous in particular for magnetic resonance units, in which many different frequencies occur and the node points migrate as a function of frequency.

The isolating means advantageously consist of an elastic, vibration damping material, in particular an elastomer. Such materials can be produced economically in large quantities, it being possible to tailor the vibration-damping action to respective needs. They are also easy to process.

In order to be able to ensure optimum seating of the cover on the assembly in a simple manner, in one advantageous embodiment equalizing means are arranged between the cover and the assembly, to adjust the gap between the cover and the assembly.

In a further possible embodiment the cover comprises a support structure to facilitate the handling of the cover. The support structure can at the same time enhance the rigidity and therefore the stability of the form of the cover. To this end the support structure is advantageously arranged between the outer casing of the cover and the isolating means and/or integrated at least partially in certain parts of the outer casing of the cover.

BRIEF DESCRIPTION OF THE DRAWINGS

Further advantages and details of the present invention will emerge from the exemplary embodiments described below and with reference to the drawings. The examples given only represent a selection of the possible embodiments and do not restrict the invention.

FIG. 5 shows a schematic diagram of a third exemplary embodiment of the invention viewed from the front, FIG. 6 shows a schematic diagram of the third exemplary embodiment of the invention viewed from the side.

DETAILED DESCRIPTION OF THE INVENTION

Without this representing a restriction, in the following exemplary embodiments in each instance the assembly is shown in the form of a magnet unit of a magnetic resonance unit. The diagrams are not to scale.

Figure 1:
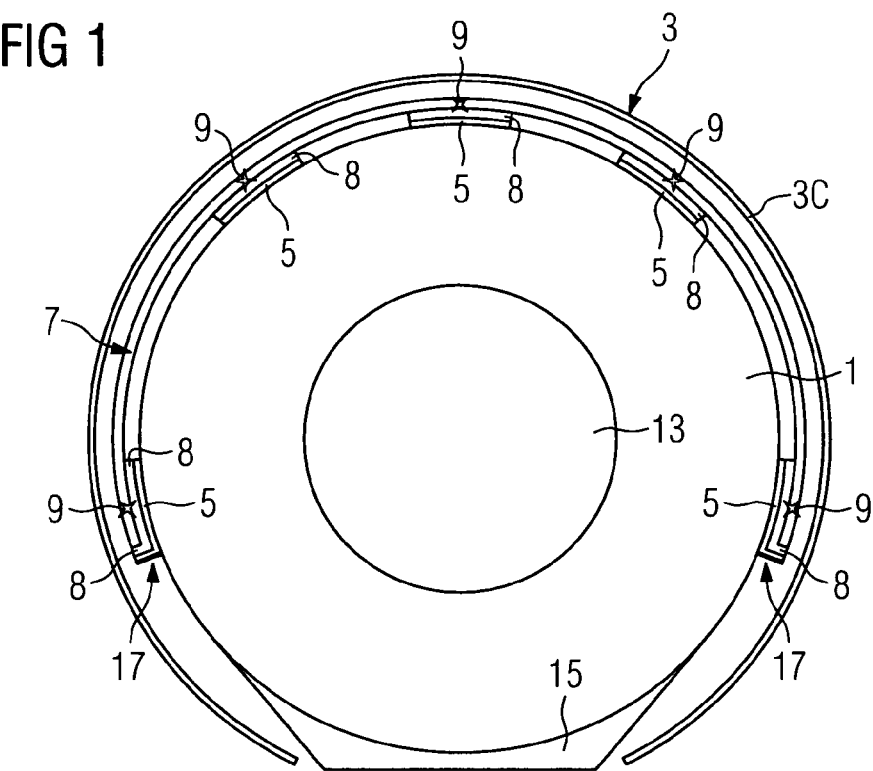
FIG. 1 shows a schematic diagram of a first exemplary embodiment of the invention viewed from the front.

FIG. 1 shows a first embodiment of the invention viewed from the front. The vibration-generating assembly 1 is shown schematically as a simplified hollow cylindrical magnet unit 1, comprising at least a main magnet and gradient coils (not shown), with an opening 13 and a foot 15, which is covered with a cover 3 on the outside. In the selected diagram a front cover of the assembly 1 is not shown, for purposes of clarity.

In this embodiment the cover 3 comprises a multi-part outer casing 3A,3B,3C and a support structure 7, tensioned over the assembly 1 like headphones. The support structure 7 in turn comprises support surfaces 8, for example configured as plates, which maximize the bearing surface between the isolating means 5 and the support structure 7. To this end the support surfaces 8 and the corresponding isolating means 5 are where possible of the same form at the surfaces where they meet. This makes optimum use of the damping action of the isolating means 5.

In this exemplary embodiment the cover 3 can be assembled easily on the assembly 1 and assembly times are shortened significantly. To this end the support structure 7 is simply tensioned over the assembly 1 and the cover is secured to the support structure 7 using equalizing means 9.

The support structure 7 is advantageously manufactured from fiber-reinforced plastics. For example the part of the support structure 7 spanning the assembly is manufactured from carbon fiber reinforced plastics, ensuring a high level of tensioned rigidity. In contrast the support surfaces 8 can advantageously be made of glass fiber reinforced plastics, as here a high level of bearing strength is advantageous rather than tensioned rigidity. In this instance the support structure 7 can also be manufactured simply in one process wet-in-wet from the various fiber reinforced plastics. Also support structures and support surfaces made of fiber reinforced plastics have an advantageously light weight. The dimensions of the support structure can thus be reduced to the essential, which in turn facilitates assembly.

In any case the material of the support structure 7 should provide adequate rigidity and optionally spring tension, should not be magnetic and where possible should be easy to process. Stainless steel, spring steel and aluminum are therefore possible further materials.

The isolating means 5 are arranged over a large area between the support structure 7 of the cover 3 and the assembly 1. The isolating means 5 consist for example of rectangular elastic, vibration-damping elastomer facings measuring around 10 cm×10 cm to 20 cm×20 cm or larger. In the case of smaller assemblies a smaller format and other, for example rounded, forms may be expedient for the isolating means.

The isolating means 5 are hereby supported in such a manner that they float in relation to the assembly 1 and/or the support structure 7 of the cover 3, in order to enhance the damping action and facilitate assembly and take on the form of the assembly.

Depending on the type of assembly 1 and the vibrations generated, an elastomer with suitable damping characteristics can be selected for the isolating means 5.

For optimum seating of the cover 3 around the assembly 1 the support structure 7 comprises equalizing means 9, by means of which the outer casing of the cover 3 is secured to the support structure 7. The equalizing means 9 also allow fine positioning of the cover 3 around the assembly 1, for example the centering of an inlet opening of the cover 3 (not shown) on the opening 13 of the magnet unit. The equalizing means 9 also allow the equalization of tolerances of the assembly 1 and cover 3. The equalizing means 9 are for example plates with longitudinal holes, bolts with knurled nuts, eccentric fast-action clamps, brackets, plates of varying thickness, which are inserted for example between the support surfaces and the isolating means or other known position adjustment means.

Equalizing means that can be closed and opened quickly and easily, for example the fast-action clamps mentioned above, also allow fast and simple assembly and disassembly, for example for service work.

In the exemplary embodiment shown the support structure 7 abuts for further rigidity, in particular to prevent the support structure 7 tipping, against support means 17 attached permanently to the assembly 1—in this instance in the form of flanges. Isolating means 5 are arranged between the support means 17 and the support structure here too. Further options for support means 17 are for example pedestals, brackets or rails. Such support means 17 are often already present on the assembly 1, in particular on magnet units, by the nature of the structure, so no additional outlay is required.

Figure 2:
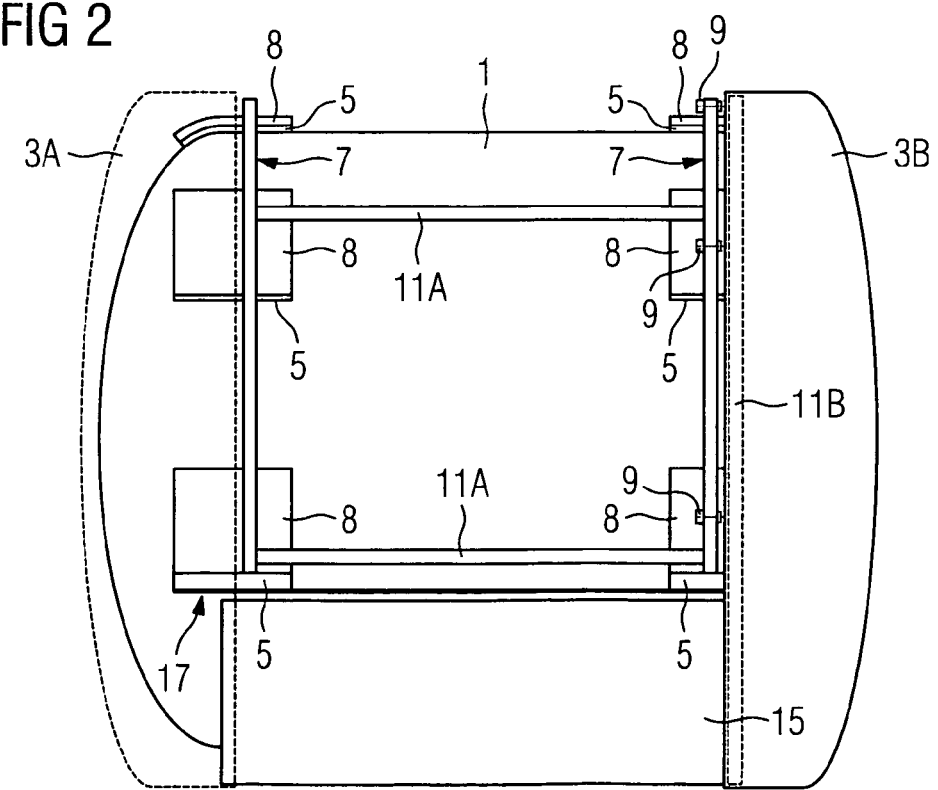
FIG. 2 shows a schematic diagram of the first exemplary embodiment of the invention viewed from the side.

FIG. 2 shows the embodiment from FIG. 1 viewed from the side, with identical parts having identical reference characters. For greater clarity the side parts 3C of the cover 3 and a front part 3A of the cover 3 are not shown. The position of the front part 3A of the cover 3 is shown with a broken line. A rear part 3B of the cover 3 with a reinforcing strut 11B (shown with a broken line) fitted below the rear part 3B is shown on the right. The front part 3A essentially has the same structure as the rear part 3B.

The reinforcing strut 11B is for example connected permanently to the rear cover 3B, being for example laminated in in the manner of a profile or being secured by means of securing means, and allows stable anchoring of the equalizing means 9, which connect the reinforcing strut 11B of the rear cover 3B to the support frame 7. Such a reinforcing strut 11B is not necessary, if the front cover 3A and rear cover 3B themselves have adequate rigidity and can be secured to the support structure 7. If precise positioning of the front part 3A and rear part 3B is not necessary, these parts 3A and 3B can also simply be placed on the assembly 1 or the side parts of the cover 3 or be suspended therefrom.

The side parts of the cover 3 can also be reinforced by reinforcing struts 11A, which reinforce the support structure 7 and optionally serve as spacers at the same time. The lateral reinforcing struts 11A can hereby either connect the support structures 7 to a support frame as shown, which can facilitate the handling of the cover 3 or can be secured to or integrated in the outer casing 3C of the cover 3 like the reinforcing strut 11B. The lateral reinforcing struts 11A are also not necessary, if the side parts 3C of the cover 3 already have adequate rigidity. The side parts of the cover 3 themselves then brace the support structure 7 and therefore also the cover 3.

To improve the fixing of the cover 3 to the assembly 1, both the isolating means 5 and the associated support surfaces 8 are tailored to the form of the assembly 1. In the example shown it can be seen on the left for example that isolating means 5 and support surfaces 8 follow the pattern of the assembly 1 precisely and therefore assist with fixing in the longitudinal direction.

In the exemplary embodiment shown the assembly 1 has ten isolating means 5 with associated support surfaces 8. This number is only by way of example. The actual number of isolating means 5 and support surfaces 8 is determined as required in each instance. It is also possible for example to use continuous isolating means 5 in the circumference of the assembly and corresponding support surfaces 8.

The isolating means 5 are hereby supported in such a manner that they float for example in relation to the assembly 1 but are secured, for example adhered, to the support surfaces 8, which facilitates handling and ensures a maximum bearing surface between the isolating means 5 and support surfaces 8. The isolating means 5 can however also simply be positioned so that they float both below the assembly 1 and below the support surfaces 8, allowing a high level of variability. Or the isolating means 5 are secured to the assembly 1 and supported so that they float in relation to the support surfaces 8.

In any case the vibration isolation over a large area ensures a high degree of vibration damping and the assembly 1 can be operated with very low noise emissions.

Further variants are also possible for the support structure 7. It is possible for example to execute the support structure so that it is flat and is tensioned around the assembly 1 like a tube clip, instead of being in the shape of headphones as shown above. This would ensure a high level of securing reliability, since tolerances of the assembly 1 and isolating means 5 for example would have less influence on such a tube clip type support structure 7. Stainless steel and therefore a recyclable material could also be used for example. It should however be ensured that the isolating means 5 are not too compressed by a tube clip type support structure 7.

Figure 3:
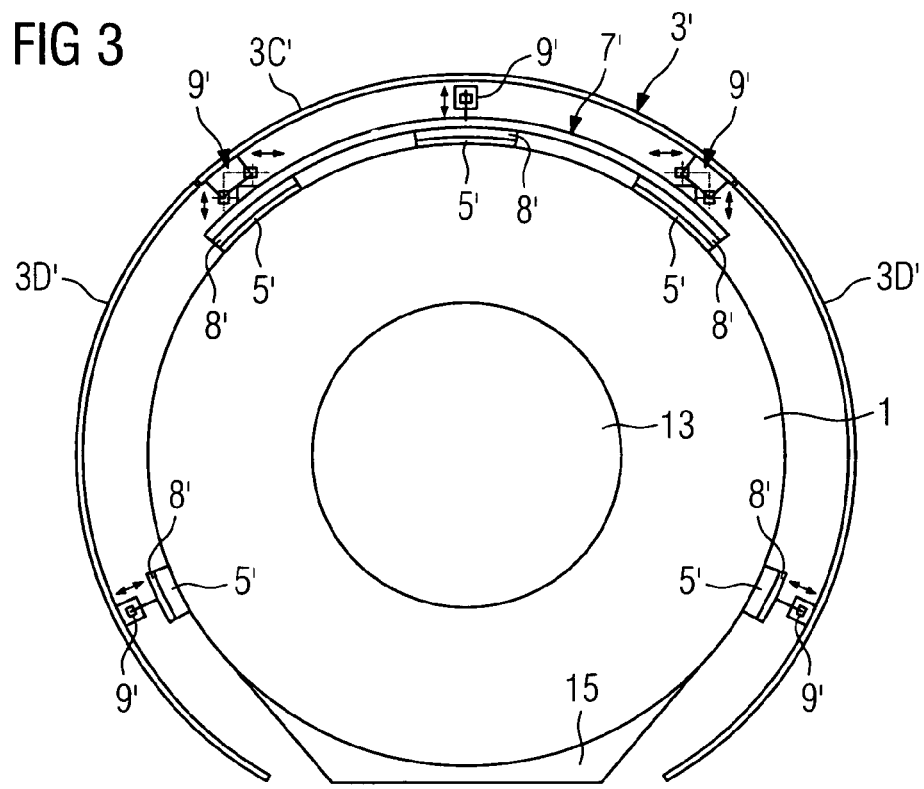
FIG. 3 shows a schematic diagram of a second exemplary embodiment of the invention viewed from the front.
Figure 4:
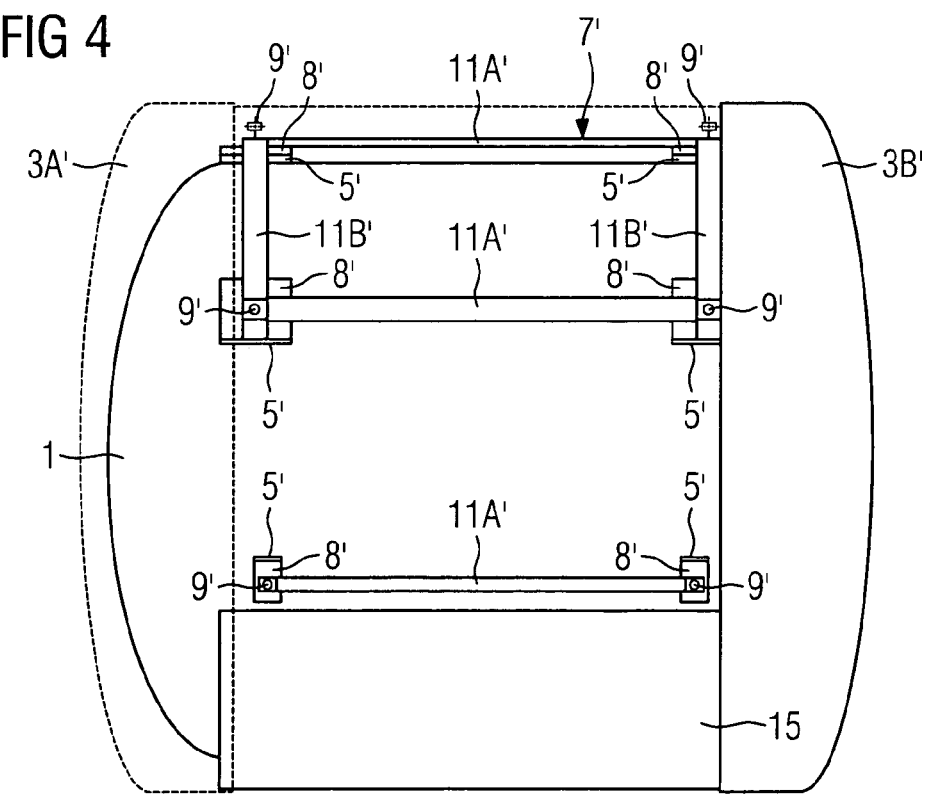
FIG. 4 shows a schematic diagram of the second exemplary embodiment of the invention viewed from the side.

FIGS. 3 and 4 show a further exemplary embodiment of the invention viewed from the front and side.

As in the first exemplary embodiment the vibration-generating assembly 1 is again shown as a simplified hollow cylindrical magnet unit 1 with an opening 13 and a foot 15, being covered on the outside with a cover 3'. Again the front cover of the assembly 1' is not shown in FIG. 3 and side parts of the cover 3' and the front cover 3A' are not shown in FIG. 4, for greater clarity. FIG. 4 again shows the position of the front part 3A' of the cover 3' with broken lines.

In this exemplary embodiment the cover 3' comprises a support structure 7', which is smaller and therefore more manageable than in the first exemplary embodiment.

The support structure 7' is not tensioned over the assembly 1' but simply rests on the assembly 1' by way of isolating means 5' and is held on the assembly 1' by the weight of the cover 3' and support structure 7'.

The support structure 7' comprises support surfaces 8', which maximize the bearing surface between the isolating means 5' and the support structure 7' for optimum damping action on the part of the isolating means 5'. The isolating means 5' are arranged between the support surfaces 8' and the assembly 1' and as in the first exemplary embodiment are supported in such a manner that they float in relation to the assembly 1' and/or the support surfaces 8'.

The cover 3' is secured to the support structure 7' by means of equalizing means 9', thereby allowing precise adjustment of the position of the cover 3' in relation to the assembly 1' (arrows). A selection of possible equalizing means 9' is given above in the description of FIGS. 1 and 2 and these can of course also be used in combination.

To facilitate assembly the cover 3' is divided into a number of parts. For example the cover 3' can be divided into a front part 3A', a rear part 3B' and upper and lower side parts 3C' and 3D'.

To assemble the cover 3' on the assembly 1', the support structure 7' is for example positioned on the assembly 1' at the top and an upper side part 3C' of the cover 3' is secured to the support structure above it by means of the equalizing means 9'. Further side parts 3D' can be suspended in the first cover part 3C' or reinforcing struts 11A' simply, for example by means of hinges, brackets, latching bolts, etc. It is also possible to suspend the side parts 3D' in the front and rear parts 3A' and 3B'. The cover part 3C' is optionally configured so that a supply tower (not shown) is or can easily be integrated in the inward and outward lines, for example a quench line and supply lines.

To stabilize the lower side parts 3D' of the cover 3' further, individual smaller support surfaces 8' can be attached with equalizing means 9', for example in the lower region of the side parts 3D', which in turn hold the side parts 3D' away from the assembly 1' by way of isolating means 5', it being possible to adjust the gap by way of the equalizing means 9'.

The front and rear parts 3A' and 3B' are either likewise secured by way of equalizing means 9' to the support structure 7' or are simply suspended from or placed on the other cover parts 3C' and 3D' or the assembly 1'.

To reinforce the cover 3' it is possible, as in the first exemplary embodiment, to attach or integrate reinforcing struts 11A' und 11B' to or in the support structure and/or the cover 3'.

The materials for the isolating means 5' and the support structure 7' can be selected as in the first exemplary embodiment. However since the support structure 7' here does not have to have a spring tensioning function, stainless steel can also be used as the material.

The form of the isolating means 5' and the associated support surfaces 8' can again be tailored individually to requirements. In particular it is also possible to have for example a large elastomer plate in the upper region as the isolating means 5', running over the entire length of the assembly 1'.

FIGS. 5 and 6 show a further exemplary embodiment of the invention viewed from the front and side.

The vibration-generating assembly 1 is again shown as a simplified hollow cylindrical magnet unit 1 with an opening 13 and a foot 15, being covered on the outside with a cover 3". The front part 3A" of the cover 3" of the assembly 1" is not shown in FIG. 5 as side parts of the cover 3" and the rear part 3B" of the cover 3" are not shown in FIG. 6, for greater clarity. FIG. 6 shows the position of the rear part 3B" of the cover 3" with broken lines.

This exemplary embodiment does not have a support structure. Instead in the upper region of the assembly 1" the cover 3" is essentially supported by isolating means 5" in the form of at least one larger, thicker damping layer, made of elastomer for example. The dimensions of the isolating means 5" are essentially a function of the dimensions of the assembly. In the case of a magnet unit as the assembly 1, 20 to 50 mm or more is suggested for the thickness of the damping layer. If there is just a single damping layer as the isolating means 5", this should at least cover roughly the upper third of the assembly. If a number of damping layers are used, their dimensions can be for example in the order of 1500 mm×120 mm.

The position of the cover 3" can be adjusted in this instance for example inserting possibly smaller plates, for example also made of elastomer or even plastic, below the necessary points in each instance.

The front and rear parts 3A" and 3B" of the cover can be attached as in the first two exemplary embodiments.

Assembly again takes place in essentially the same manner as for the second exemplary embodiment with the cover 3" here being positioned directly on the large isolating means 5" arranged at the top, with no support structure in between. Or the cover 3" itself, in particular the side parts 3C" and 3D", which can also be manufactured as a single part, is manufactured from a material, e.g. carbon fiber reinforced plastics, which has an adequate tensioning force so that the cover can be tensioned on the assembly 1" as in the first exemplary embodiment but here directly by way of the isolating means 5".

In the lower region of the side parts of the cover 3" additional support surfaces 8" can be fixed, as already described in the second exemplary embodiment, by way of equalizing means 9", said additional support surfaces 8" holding the cover 3" at an adjustable distance from the assembly 1" by way of additional isolating means 5". This helps to stabilize the cover. Reinforcing struts 11A" for further reinforcement can also be attached at these points.

Alternatively the lower region of the side parts of the cover 3" can also be stabilized by further isolating means in the form of large damping layers like the ones positioned at the top.

The exemplary embodiments should only be seen as examples. Further possible embodiments will result for example from any combination of the methods for vibration damping set out in the three exemplary embodiments listed.

The invention claimed is:

1. A vibration-generating device, comprising:
   a cover;
   an isolating device arranged between the cover and the vibration-generating device that reduces a propagation of vibrations originated from the vibration-generating device to an outer casing of the cover and is not permanently adhered to both the cover and the vibration-generating device so that the isolating device is supported to float with respect to the vibration-generating device or the cover; and
   a support surface having a same form with the isolating device to optimally using damping action of the isolating device.

2. The vibration-generating assembly as claimed in claim 1, wherein the isolating device comprises a large bearing surface on which the cover rests.

3. The vibration-generating device as claimed in claim 1, wherein the isolating device comprises an elastic and vibration-damping material.

4. The vibration-generating device as claimed in claim 3, wherein the elastic and vibration-damping material is an elastomer.

5. The vibration-generating device as claimed in claim 1, wherein at least a part of the cover is tensioned over the vibration-generating device and holds the cover on the vibration-generating device.

6. The vibration-generating device as claimed in claim 1, wherein an equalizing device is arranged between the cover and the vibration-generating device that adjusts a gap between the cover and the vibration-generating device.

7. The vibration-generating device as claimed in claim 6, wherein the support surface is attached on the equalizing device.

8. The vibration-generating device as claimed in claim 1, wherein the cover comprises a support structure arranged between the outer casing of the cover and the isolating device to facilitate handling of the cover.

9. The vibration-generating device as claimed in claim 8, wherein the support structure maximizes a bearing surface between the isolating device and the support structure.

10. The vibration-generating device as claimed in claim 8, wherein at least a part of the support structure abuts against the vibration-generating device.

11. The vibration-generating device as claimed in claim 8, wherein the support structure comprises a fiber reinforced plastic.

12. The vibration-generating device as claimed in claim 11, wherein the fiber reinforced plastic comprises a carbon fiber reinforced plastic.

13. The vibration-generating device as claimed in claim 11, wherein the fiber reinforced plastic comprises a glass fiber reinforced plastic.

14. The vibration-generating device as claimed in claim 8, wherein the support structure comprises a reinforcing strut to reinforce the cover.

15. The vibration-generating device as claimed in claim 1, wherein the support surface is attached on the support structure.

16. The vibration-generating device as claimed in claim 1, wherein the cover comprises a plurality of cover parts.

17. The vibration-generating device as claimed in claim 1, wherein the vibration-generating device is a magnet unit of a magnetic resonance unit.

18. A method for reducing a propagation of vibrations originated from a vibration-generating device to an outer casing of a cover of the vibration-generating device, comprising:
   arranging an isolating device between the cover and the vibration-generating device being not permanently adhered to both the cover and the vibration-generating device;
   supporting the isolating device to float with respect to the vibration-generating device or the cover; and
   providing a support surface having a same form with the isolating device to optimally using damping action of the isolating device.

* * * * *